US012589121B2

(12) United States Patent
Filho et al.

(10) Patent No.: US 12,589,121 B2
(45) Date of Patent: Mar. 31, 2026

(54) METHOD FOR OBTAINING OCCLUSIVE BIOLOGICAL DRESSING, OCCLUSIVE BIOLOGICAL DRESSING, USE THEREOF AND KIT

(71) Applicants: Universidade Federal do Ceará, Fortaleza (BR); Edmar Maciel Lima Júnior, Fortaleza (BR)

(72) Inventors: Manoel Odorico De Moraes Filho, Fortaleza (BR); Maria Elisabete Amaral De Moraes, Fortaleza (BR); Felipe Augusto Rocha Rodrigues, Fortaleza (BR); Carlos Roberto Koscky Paier, Fortaleza (BR)

(73) Assignees: UNIVERSIDADE FEDERAL DO CEARÁ (BR); Edmar Maciel Lima Júnior (BR)

( * ) Notice: Subject to any disclaimer, the term of this patent is extended or adjusted under 35 U.S.C. 154(b) by 879 days.

(21) Appl. No.: 17/294,308

(22) PCT Filed: Nov. 14, 2019

(86) PCT No.: PCT/BR2019/050494
§ 371 (c)(1),
(2) Date: May 14, 2021

(87) PCT Pub. No.: WO2020/097710
PCT Pub. Date: May 22, 2020

(65) Prior Publication Data
US 2022/0008483 A1 Jan. 13, 2022

(30) Foreign Application Priority Data
Nov. 14, 2018 (BR) ......................... 102018073510-1

(51) Int. Cl.
*A61K 35/60* (2006.01)
*A61P 17/02* (2006.01)
*F26B 5/06* (2006.01)

(52) U.S. Cl.
CPC .............. *A61K 35/60* (2013.01); *A61P 17/02* (2018.01); *F26B 5/06* (2013.01)

(58) Field of Classification Search
CPC ..................................................... A61K 35/60
See application file for complete search history.

(56) References Cited

U.S. PATENT DOCUMENTS

| | | | |
|---|---|---|---|
| 8,226,715 | B2 | 7/2012 | Hwang et al. |
| 11,135,337 | B2 | 10/2021 | Junior et al. |
| 2011/0244054 | A1 | 10/2011 | Sigurjonsson et al. |
| 2016/0287643 | A1 | 10/2016 | Lai et al. |
| 2021/0402057 | A1 | 12/2021 | Filho et al. |

FOREIGN PATENT DOCUMENTS

| | | | |
|---|---|---|---|
| BR | 102016007036 A2 | 10/2016 | |
| BR | 102015021435 A2 | 3/2017 | |
| CN | 1096458 A | * 12/1994 | |
| CN | 108355171 A | 8/2018 | |
| CN | 108355172 A | 8/2018 | |
| CN | 109078222 A | 12/2018 | |
| WO | 2011042794 A2 | 4/2011 | |
| WO | 2013144727 A2 | 10/2013 | |
| WO | 2017035615 A1 | 3/2017 | |
| WO | 2020097711 A1 | 5/2020 | |

OTHER PUBLICATIONS

Billingham, R. E. & Medawar, P.B. The freezing, drying and storage of mammalian skin. Journal of Experimental Biology. 1952. vol. 29, pp. 454-468 (Year: 1952).*

Machine trasnlation of CN1096458A, 6 pages. (Year: 1994).*

Billingham, R.E. & Medawar, P.B., "The freezing, drying and storage of mammalian skin," Journal of Experimental Biology, 1952, vol. 29, pp. 454-468.

Abbott, W.M. & Hembee, U.S., "Absence of antigenicity in freeze-dried skin allografts," Cryobiology, 1970, vol. 6, No. 5, pp. 416-418.

Abbott, W.M. & Pappas, A.M., "Comparative studies on fresh and preserved skin: fundamental biologic differences in behavior as grafts," Ann Surg., 1970, vol. 172., No. 5, pp. 781-786.

Alves, Ana Paula Negreiros Nunes, et al., "Microscopic evaluation, histochemical study and analysis of tensiometric properties of the Nile Tilapia skin," Rev Bras Queimaduras, 2015, vol. 14(3), 8 pages; Abstract in English.

Alves, Ana Paula Negreiros Nunes, et al., "Study of tensiometric properties, microbiological and collagen content in nile tilapia skin submitted to different sterilization methods," Cell Tissue Bank, 2018, 10 pages.

Azevedo-Santos, Valter Monteiro de, et al., "Growing, losing or introducing? Cage aquaculture as a vector for the introduction of non-native fish in Furnas Reservoir, Minas Gerais, Brazil," Neotropical Ichthyology, 9(4), 2011 Sociedade Brasileira de Ictiologia, 5 pages.

Barbosa, H.R., et al., "Counting of viable cluster-forming and non cluster-forming bacteria: a comparison between the drop and the spread methods," Journal of Microbiological Methods 22, 1995, 12 pages.

Bezerra, et al., "Tilapia Fish Skin: a new biological graft in gynecology," Rev Med UFC, 2018, abr-Jun. 58(2), 3 pages.

(Continued)

*Primary Examiner* — Qiuwen Mi
(74) *Attorney, Agent, or Firm* — Abel Schillinger, LLP

(57) ABSTRACT

The present invention describes a method for obtaining freeze-dried tilapia skin, comprising the steps of cleaning by scraping, washing with physiological saline solution and trimming the edges of the skin; incubation with biocompatible detergent in a sterile recipient and rinsing, incubation with bactericidal agent in sterile recipient and rinsing, incubating with detoxifying solution and rinsing, incubation with antibiotics, rinsing and freezing, cold freeze-drying, vacuum sealing and sterilization, and more specifically the present invention includes the use of tilapia skin to prepare a remedy for treating lesions in humans and animals. The present invention relates to the fields of pharmacy, medicine, dentistry, veterinary medicine, chemistry, biotechnology and tissue engineering.

10 Claims, No Drawings

(56) References Cited

OTHER PUBLICATIONS

Costa, Bruno Almeida, et al., "Evaluation of Reduction in the Use of Analgesics by Outpatient Patients in a Center of Reference Burns in Fortaleza Com Application of Tilapia Skin as a Dressing Occlusive Biological in the Treatment of Second Degree Surface Burns", Encontros Universitarios da UFC. 2017, 2, 3 pages; Abstract in English.

Lima-Junior, Edmar Maciel, et al., "Chracterization of the microbiota of the skin and oral cavity of Oreochromis niloticus," J. Health Biol Sci 2016, 4(3), 5 pages.

Lima-Junior, Edmar Maciel, "Innovative technologies: the use of Nile tilapia skin in the treatment of burns and wounds," Rev Bras Queimaduras, 2017, 16(1), 2 pages; English language document unavailable.

Lima-Junior, Edmar Maciel, et al., "The use of tilapia skin (Oreochromis niloticus), as an occlusive biological dressing, in the treatment of burn wounds," Rev Bras Queimaduras, 2017, 16(1), 8 pages; Abstract in English.

"Queiroz, Julio Ferraz de, et al., ""A Embrapa e a Aqüicultura Demandas e Prioridades de Pesquisa,"" Embrapa Informacao Technolgica Brasilia, DF, 2002, 38 pages (English language document unavailable)< https://www.alice.cnptia.embrapa.br/bitstream/doc/108115/1/seatexto11.pdf >".

Ramos, IP., "Influence of cage fish farming on the diet of dominant fish species of a Brazilian reservoir (Tietê River, High Parana River basin)," Acta Limnol. Bras., 2008, vol. 20, No. 3, 9 pages.

Gilbert, Thomas W., et al., "Decellularization of tissues and organs," Biomaterials, V. 27,No. 19, 2006, 9 pages.

Munnelly, Amy E., et al., "Porcine vena cava as an alternative to bovine pericardium in bioprosthetic percutaneous heart valves," Biomaterials 33, 2012, 8 pages.

Badylak, Stephen F., "The extracellular matrix as a scaffold for tissue reconstruction," Seminars in Cell & Developmental Biology, vol. 13, From the Department of Biomedical Engineering, Purdue University, 2002, 7 pages.

Badylak, Stephen F., et al., "Extracellular matrix as a biological scaffold material: Structure and function," Acta Biomaterials, 5, 2009, 13 pages.

Witt, J., Mertsch, S., Borrelli, M., Dietrich, J., Geerling, G., Schrader, S., Spaniol, K., Decellularised conjunctiva for ocular surface reconstruction, Acta Biomaterialia (2017), 36 pages doi:< https://doi.org/10.1016/j.actbio.2017.11.054 >.

Vastine, MD, David W., et al., "Reconstruction of the Periocular Muscous Membrane by Autologous Conjunctival Transplantation," American Academy of Ophthalmology, Sep. 1982, vol. 89, No. 9, 10 pages.

Badylak, Stephen F., "The extracellular matrix as a biologic scaffold material," Biomaterials 28, 2007, 7 pages.

Mazza, Giuseppe, et al., "Rapid production of human liver scaffolds for functional tissue engineering by high shear stress oscillation-decellularization," Scientific Reports, Jul. 17, 2017, 14 pages.

Haupt, Jessica, et al., "Detergent-based decellularization strategy preserves macro- and microstructure of heart valves," Interactive CardioVascular and Thoracic Surgery, Advance Access Publication: Oct. 9, 2017, 7 pages.

Xing, Qi, et al., "Decellularization of Fibroblast Cell Sheets for Natural Extracellular Matrix Scaffold Preparation," Department of Engineering, Tissue Eng Part C Methods, vol. 21, No. 1, 2015, 45 pages.

Mendoza-Novelo, Birzabith, et al., "Decellularization of pericardial tissue and its impact on tensile viscoelasticity and glycosaminoglycan content," Acta Biomaterialia 7, 2011, 8 pages.

Sullivan, David C., et al., "Decellularization methods of porcine kidneys for whole organ engineering using a high-throughput system," Biomaterials 33, 2012, 9 pages.

Gilpin, Sarah Elizabeth, et al., "Perfusion decellularization of human and porcine lungs: Bringing the matrix to clinical scale," The Journal of Heart and Lung Transplantation, vol. 33, Issue 3, p. 298-308, Published Oct. 28, 2013, 11 pages.

Petersen, Thomas H., et al., "Matrix Composition and Mechanics of Decellularized Lung Scaffolds," Cells Tissues Organs, 2012, vol. 195, No. 3, 10 pages.

Petersen, Thomas H., et al., "Tissue-Engineered Lungs for in Vivo Implantation," Science, Jul. 30, 2010, vol. 329, 5 pages.

Gilpin, Anna, et al., "Decellularization Strategies for Regenerative Medicine: From Processing Techniques to Applications," Hindawi, BioMed Research International, vol. 2017, Article ID 9831534, 14 pages.

Kasimir, Marie-Theres, et al., "The decellularized porcine heart valve matrix in tissue engineering," Thrombogenicity of decellularized heart valves, 2005, 94, 6 pages.

Paz, Ana C., et al., "Tissue Engineered Trachea Using Decellularized Aorta," Journal of Bioengineering and Biomedical Science, 2011, 7 pages.

Azhim, A., et al., "The use of sonication treatment to decellularize aortic tissues for preparation of bioscaffolds," Journal of Biomaterials Applications, 2014, vol. 29 (1), 12 pages.

Wu, Xiujuan, et al., "Genipin-Crosslinked, Immunogen-Reduced Decellularized Porcine Liver Scaffold for Bioengineered Hepatic Tissue," Tissue Eng Regen Med 2015, 12 (6), 10 pages.

Powell, Heather M., et al., "EDC cross-linking improves skin substitute strength and stability," Biomaterials 27, 2006, 7 pages.

Zhai, Wanyin, et al., "Crosslinking of decellularized porcine heart valve matrix by procyanidins," Biomaterials 27, 2006, 7 pages.

Chen, Zhengjian, et al., "The effect of procyanidine crosslinking on the properties of the electrospun gelatin membranes," Biofabrication 4, 2012, 12 pages.

Koch, Holger, et al., "Xenogenic Esophagus Scaffolds Fixed with Several Agents: Comparative In Vivo Study of Rejection and Inflammation," Hindawi Publishing Corporation, Journal of Biomedicine and Biotechnology, vol. 2012, Article ID 948320, 12 pages.

Hussein, Kamal H., et al., "New insights into the pros and cons of cross-linking decellularized bioartificial organs," Int J. Artif Organs, 2017, 40(4), 6 pages.

Wassenaar, Jean W., et al., "Modulating In Vivo Degradation Rate of Injectable Extracellular Matrix Hydrogels," Journal of Materials Chemistry B, 2016, 21 pages.

Williams, Corin, et al., "Cardiac Extracellular Matrix-Fibrin Hybrid Scaffolds with Tunable Properties for Cardiovascular Tissue Engineering," Acta Biomater. 2015, 14, 26 pages.

Sheridan (Tissue Engineering 2013, vol. 19. No. 12, pp. 981-990.

IAEA-TECDOC-539, Guidelines for Industrial Radiation Sterilization of Disposable Medical Products, Cobalt-60 Gamma Irradiation, International Atomic Energy Agency, 1990, Excerpt section 4.2.3, p. 15.

Dai, Z., Ronholm, J., Tian, Y., Sethi, B., & Cao, X. (2016). Sterilization techniques for biodegradable scaffolds in tissue engineering applications. Journal of Tissue Engineering, 7, 2041731416648810. DOI: 10.1177/2041731416648810.

Nivelle, R., Gennotte, V., Kalala, E. J. K., Ngoc, N. B., Muller, M., Mélard, C., & Rougeot, C. (2019). Temperature preference of Nile tilapia (Oreochromis niloticus) juveniles induces spontaneous sex reversal. PLoS One, 14(2), e0212504. DOI: 10.1371/journal.pone.0212504.

Nobrega, R. O., Banze, J. F., Batista, R. O., & Fracalossi, D. M. (2020). Improving winter production of Nile tilapia: What can be done? Aquaculture Reports, 18, 100453. DOI: 10.1016/j.aqrep.2020.100453.

Leonard, J. N., & Skov, P. V. (2022). Capacity for thermal adaptation in Nile tilapia (Oreochromis niloticus): Effects on oxygen uptake and ventilation. Journal of Thermal Biology, 105, 103206. DOI: 10.1016/j.jtherbio.2022.103206.

Liang, H. C., Chang, Y., Hsu, C. K., Lee, M. H., & Sung, H. W. (2004). Effects of crosslinking degree of an acellular biological tissue on its tissue regeneration pattern. Biomaterials, 25(17), 3541-3552. https://doi.org/10.1016/j.biomaterials.2003.09.109.

Delgado, L. M., Bayon, Y., Pandit, A., & Zeugolis, D. I. (2015). To cross-link or not to cross-link? Cross-linking associated foreign

(56) References Cited

OTHER PUBLICATIONS body response of collagen-based devices. Tissue Engineering. Part B, Reviews, 21(3), 298-313. https://doi.org/10.1089/ten.TEB.2014.0290.

Grabska-Zielińska S. Cross-Linking Agents in Three-Component Materials Dedicated to Biomedical Applications: A Review. Polymers. 2024; 16(18):2679. https://doi.org/10.3390/polym16182679.

* cited by examiner

METHOD FOR OBTAINING OCCLUSIVE BIOLOGICAL DRESSING, OCCLUSIVE BIOLOGICAL DRESSING, USE THEREOF AND KIT

The present invention describes the method for obtaining freeze-dried tilapia skin comprising the steps of cleaning by scraping, washing with physiological saline solution, and trimming the edges of the skin; incubation with biocompatible detergent in sterile recipient and rinsing, incubation with bactericidal agent in sterile recipient and rinsing, incubating with detoxifying solution and rinsing, incubation with antibiotics, rinsing and freezing, cold freeze-drying, vacuum sealing and sterilization, more specifically the present invention comprises the use of tilapia skin to prepare a remedy for treating lesions in humans and animals. The present invention relates to the fields of pharmacy, medicine, dentistry, veterinary medicine, chemistry, biotechnology and tissue engineering.

BACKGROUND OF THE INVENTION

Currently human and veterinary medicine in Brazil does not comprise any alternative for heterologous temporary skin cover (of animal origin), as part of treatment for burns and wounds. In developed countries, particularly in the United States, industrialized extracellular matrixes have been used with this purpose and in large scale, for several decades. The importation of this product to Brazil has never shown to be commercially viable, considering the high cost and the economic reality of the country.

In the search for the state of the art in scientific and patent literature, the following documents were found, which deal with the theme:

Document BR1020150214359A2 differs from the present invention by being processed in glycerol and sterilized by gamma radiation. This product that is maintained in glycerol requires storage under refrigeration. Further, the document does not cite the possibility of freeze-drying.

LIMA-JUNIOR EM, PICOLLO NS, MIRANDA MJB, RIBEIRO WLC, ALVES APNN, FERREIRA G E, et al. Uso da pele de tilápia (Oreochromis niloticus) como curativo biológico oclusivo no tratamento de queimaduras. Rev Bras Queimaduras, 2017; 16(1):10-17. The document differs from the present invention by using glycerol in the skin decontamination, storage of the product in refrigerator and possibility of toxic residues from the glycerol. Further, this document does not use the steps of freeze-drying in the method.

ALVES, APNN; LIMA VERDE, MEQ; FERREIRA JÚNIOR, AEC; SILVA, PGB.; FEITOSA, VP; LIMA JÚNIOR, EM; MIRANDA, MJB; MORAES FILHO, MO. Avaliação microscôpica, estudo histoquîmico e análise de propriedades tensiomêtricas da pele de tilapia do Nilo. Rev Bras Queimaduras. 2015; 14(3):203-10.

ALVES, APNN; LIMA-JUNIOR, EM; PICOLLO, NS; MIRANDA, MJB; VERDE, MEQL; FERREIRA-JÚNIOR, AEC; SILVA, PGB; FEITOSA, VP; DE BANDEIRA, TJPG; MATHOR, MO; DE MORAES, MO. Study of tensiometric properties, microbiological and collagen content in Nile tilapia skin submitted to different sterilization methods. Cell Tissue Bank. 2018; 18(1):1-10

AZEVEDO-SANTOS, V. M.; RIGOLIN-SÁ, O.; PELICICE, F. M. Growing, losing or introducing Cage aquaculture as a vector for the introduction of non-native fish in Furnas Reservoir, Minas Gerais, Brazil. Neotropical Ichthyology, 9: 915-919, 201 1.

BARBOSA HR, RODRIGUES MFA, CAMPOS CC, CHAVES ME, NUNES I, JULIANO Y, NOVO NF. Counting of viable cluster-forming and non cluster-forming bacteria: A comparison between the drop and the spread methods. J Microbiol Methods 1995; 22:39-50.

BEZERRA, LR; MORAES, MO; BRUNO, ZV; LIMA JÚNIOR, EM; ALVES, AP; BILHAR, AP; DIAS, MTPM; RIOS, LC. Tilapia fish skin: a new biological graft in gynecology. Rev Med UFC. 2018, 58 (2): 6-8

CARVALHO, E. D. Avaliação dos impactos da piscicultura em tanques-rede nas represas dos grandes tributários do alto Paraná (Tiete e Paranapanema): o pescado, a ictiofauna agregada e as condições limnolôgicas. Relatório Científico (FAPESP). Botucatu, S P. 2006. 46p.

CASTAGNOLLI, N. Aquicultura para o ano 2000. Brasilia: CNPq, 1996. 95p.

COSTA BA, LIMA-JUNIOR EM, PICOLLO NS, SILVA JR FR, MARTINS CB, DO NASCIMENTO MFA, DE MORAES MO. Avaliação da redução do uso de analgésicos por pacientes ambulatoriais de um centro de queimados de referência em fortaleza corn a aplicação da pele de tilapia como curativo biológico oclusivo no tratamento de queimaduras de segundo grau superficial. Encontros Universitários da UFC. 2017, 2: 884

LIMA-JÚNIOR, EM; BANDEIRA, TJPG; MIRANDA, MJB; FERREIRA, GE; PARENTE, EA; PICCOLO, NS & MORAES FILHO, MO. Characterization of the microbiota of the skin and oral cavity of Oreochromis niloticus. Journal of Health & Biological Sciences 2016; 4(3): 193-197.

LIMA-JUNIOR, EM. Tecnologias inovadoras: uso da pele de tilápia do Nilo no tratamento de queimaduras e feridas. Rev Bras Queimaduras. 2017; 16(1):1-2

Therefore, from what is understood from the literature searched, no documents were found that anticipated or suggested the teachings of the present invention, thus, the solution proposed herein comprises novelty and inventive activity before the state of the art.

SUMMARY OF THE INVENTION

In this manner, the present invention solves the state of the art problems from the method for obtaining freeze-dried tilapia skin, which use is in the preparation of remedies to treat lesions in humans and animals, such as second and third degree burns, acute, chronic and traumatic wounds, battlefield wounds, skin donor areas for self-grafts, vaginal and pelvic floor reconstruction, neovaginal construction, sexual reassignment in transgenders, reconstruction of nasal lining and buccal cavity, gum reconstruction, tissue rupture, dermatitises, lacerations, abrasions, bruises, necrotizing fasciitis, toxic epidermic necrolysis (TEN), Stevens-Johnson Syndrome, pressure wounds, ulcers due to venous insufficiency, vascular ulcers, diabetic or neuropathic ulcers, mixed ulcers, vasculitis wounds, gangrenous pyoderma, anal fistula, reconstruction of esophageal wall, facial reconstruction, mucormycosis. In dentistry, it can be used for filling of oral mucosa, dental cavity and alveoli.

Additionally, depending on the lesion to be treated, the freeze-dried skin of the tilapia can be used on the wounds with or without sutures and with or without bandages.

The present invention further presents the following advantages:

Absence of use of glycerol as cryoprotector in the conservation of the skin of the tilapia. The absence of glycerol eliminates the chances of pain to the patient due to eventual contamination of the wound with residue of this substance in the occlusive biological dressing.

The present invention presents in one of its objects the alternative to maintenance in glycerol as comprising the cold dehydration step (freeze-drying) of the skin of the tilapia, which reduces the activity of water on the tissue, making inviable the microbial growth, increasing the chemical stability thereof (validity) and waiving the need for the refrigeration thereof.

The non-mandatory aspect of the freeze-dried skin and vacuum packaging guarantee the reduction of the storage and transport costs of the product. The vacuum packaging of the freeze-dried skin reduces the contact of the product with the atmospheric oxygen, reducing the damages due to product oxidation.

The freeze-dried skin in the conditions that are standardized in this invention is capable of rapid macroscopic rehydration, which makes it more adequate for the use in medical, dental, and veterinary practice.

The present invention presents as inventive concept the following objects:

The present invention presents as a first object a method for obtaining freeze-dried animal skin comprising freeze-drying at a temperature in the range of $-30°$ C. to $-80°$ C., with inner pressure lower than 50 µmHg (6.66 Pa) and time from 2 to 24 h.

As a second object, there is provided the freeze-dried animal skin obtained by the method described in the first object and embodiments thereof.

In a third object there is provided the use of the freeze-dried animal skin for producing dressing materials for treatment in humans and animals comprised within the group: second and/or third degree burns, acute, chronic and traumatic wounds, battlefield wounds, skin donor areas for self-graft, vaginal and pelvic floor reconstruction, neovaginal construction, sexual reassignment for transgenders, reconstruction of nasal lining and of buccal cavity, gum reconstruction, tissue rupture, dermatitises, lacerations, abrasions, bruises, necrotizing fasciitis, toxic epidermic necrolysis (TEN), Stevens Johnson Syndrome, pressure wounds, ulcers due to venous insufficiency, vascular ulcers, diabetic ulcers or neuropathic, mixed ulcers, vasculitis wounds, gangrenous pyoderma, anal fistula, reconstruction of esophageal wall, facial reconstruction, mucormycosis, filling of oral mucosa, dental cavity and alveoli.

The present invention presents a fourth object the kit comprising the animal skin, optionally from a fish, optionally from tilapia, freeze-dried.

These and other objects of the invention will be immediately valued by those that are skilled in the art and will be described in detail as follows.

DETAILED DESCRIPTION OF THE INVENTION

The present invention provides a method for the production of freeze-dried tilapia skin, which use is in the preparation of remedies for treating wounds in humans and animals, such as second and third degree burns, acute, chronic and traumatic wounds, battlefield wounds, skin donor areas for self-graft, vaginal and pelvic floor reconstruction, neovaginal construction, sexual reassignment for transgenders, reconstruction of nasal lining and of buccal cavity, gum reconstruction, tissue rupture, dermatitises, lacerations, abrasions, bruises, necrotizing fasciitis, toxic epidermic necrolysis (TEN), Stevens Johnson Syndrome, pressure wounds, ulcers due to venous insufficiency, vascular ulcers, diabetic ulcers or neuropathic, mixed ulcers, vasculitis wounds, gangrenous pyoderma, anal fistula, reconstruction of esophageal wall, facial reconstruction, mucormycosis. In dentistry, it can be used for filling of oral mucosa, dental cavity and alveoli.

The present invention further presents the following advantages:

Absence of use of glycerol as cryoprotector in the conservation of the skin of the tilapia. The glycerol is significantly hydrophilic, making the skin absorb humidity from the environment if it is not stored in a dry location, at low temperatures, to delay the water gain. For this reason, the skin that is conserved in glycerol must mandatorily be stored in refrigerator. On the contrary, it will absorb a lot of water, which accelerates the hydrolysis reactions, favors microbial growth in case of contamination and reduces the validity/stability of the product. Further, the eventual multiplication of microorganism would use the glycerol itself as a carbon source.

The present invention presents in one of its objects the alternative to maintenance in glycerol as comprising the cold dehydration step (freeze-drying) of the skin of the tilapia, which reduces the presence of water on the tissue, making inviable the microbial growth. Further, the absence of glycerol eliminates the chances of pain to the patient due to eventual contamination of the wound with this substance due to the presence of glycerol residues in the occlusive biological dressing.

It presents the step of reduction of previous microbial growth, enabling lower dosage of radiation for the complete sterilization, which can generate damages to the skin morphology by the gamma rays. The present method is compatible with the freeze-drying and subsequent radiation, that is, it is capable of eliminating the dependence on a refrigeration step and of previously reducing the microbial load of the skin. This would require a lower dose of radiation for the complete sterilization, resulting in fewer modifications in the skin morphology due to the gamma rays used. Additionally, the new method cannot preclude the previous freeze-drying to radio-sterilization, nor must it leave toxic residues on the skin.

The decontamination method is compatible with the freeze-drying, which dehydrates without using heat and, therefore, without denaturing the skin proteins and altering the morphology thereof, necessary to the function of the biological remedy.

The method of the present application reduces the water content of the product, increasing the chemical and microbiological stability thereof, resulting in longer validity and waiving the need for its refrigeration.

The vacuum packaging of the freeze-dried skin reduces the contact of the product with the atmospheric oxygen, reducing the damages due to product oxidation.

The non-mandatory aspect of the freeze-dried skin and vacuum packaging guarantee the reduction of the storage and transport costs of the product.

The addition of a step of washing of the residues from the decontamination method increases the safety of the product, since it eliminates remains of cytotoxic contaminant chemicals.

The freeze-dried skin in the conditions that are standardized in this invention is capable of rapid macroscopic rehydration, which makes it more adequate for the use in medical and veterinary practice.

The freeze-dried tilapia skin of the present invention can be used as an occlusive remedy material, considering that it is not incorporated by the organism, nor does it become irrigated by blood vessels of the receptor individual. Therefore, after a variable period of time, the skin is totally or partially eliminated from the site of the application. For this reason the use of the term "occlusive dressing" or even "biological dressing" in view of the temporary use of the invention.

The present invention presents as a first object a method for obtaining freeze-dried animal skin comprising freeze-drying at a temperature in the range of –30° C. to –80° C., with inner pressure lower than 50 µmHg (6.66 Pa) and time from 2 to 24 h, wherein the freeze-dried skin obtained is capable of macroscopic rehydration.

In one embodiment, the rehydration occurs optionally in sterile physiological saline solution, at room temperature, by immersion in stainless steel hospital tray, wherein the volume of solution must be sufficient to immerse the skin in the physiological saline during optionally 15 minutes, without the need to agitate the tray.

In one embodiment, the animal skin is obtained preferably from fishes.

In one embodiment, the fish is optionally tilapia *Oreochromis niloticus*. In one embodiment, the method comprises the steps of:

i) cleaning and trimming the skin of the tilapia;
ii) incubation and rinse;
iii) freezing;
iv) freeze-drying;
v) vacuum sealing; and
vi) sterilization.

In one embodiment, the method comprises additionally a step vii) of rehydration of the freeze-dried animal skin.

In one embodiment, in step (i) the cleaning comprises being by mechanical scraping, followed by washing with physiological solution and trimming the edges of the skin;

In one embodiment, step (ii) comprises incubation with biocompatible detergent and rinsing; followed by incubation with bactericidal agent and rinsing; followed by incubation with a detoxifying solution and rinsing.

In one embodiment, the method occurs in sterile environment containing biocompatible detergent selected from the group that comprises 3-[(3-cholamidopropyl)dimethylammonium]-1-propanesulfonate (CHAPS), Polysorbate 20 (Tween 20), t-octylphenoxypolyethoxyethanol (Triton X-100), sodium deoxycholate or 4-nonylphenyl-polyethyleneglycol (Substitute Nonidet P 40), or a combination thereof in the range 0.001-0.5%, for 15-60 minutes, in two to five repetitions, followed by two to five incubations with sterile distilled water in the same recipient for 15-60 minutes.

In one embodiment, the incubation with bactericidal agent comprised in step (ii) occurs in a sterile recipient containing bactericidal agent in the range from 0.005 to 1.0%, (optionally 0.01%-1%) for 15-60 minutes, followed by rinsing in sterile distilled water in the same recipient for 15 to 60 minutes, in two to ten repetitions, wherein the bactericidal agents are selected from the group that comprises: chlorhexidine digluconate, sodium chlorite, cetylpyridinium chloride, chloramine T and/or sodium dichloroisocyanurate; optionally the bactericidal agent is chlorhexidine digluconate.

In one embodiment, the incubation with detoxification solution comprised in step (ii) occurs in sterile recipient containing acetic acid/acetate buffer or glycine/HCl or citric acid/citrate or monobasic sodium phosphate/dibasic sodium phosphate at 0.025-0.50 mol/L, pH 3.0-6.0, for 30-120 minutes, in two to fifteen repetitions, followed by incubation with sterile distilled water in the same recipient for 15-60 minutes, in two to ten repetitions; followed by rinsing with physiological saline solution.

In one embodiment step (iii) comprises freezing in the range from –20° C. to –196° C., during 8 to 24 h, wherein optionally liquid N2 is used in the freezing.

In one embodiment, step (iv) occurs in a freeze-dryer in a range from –30° C. to –80° C., with inner pressure lower than 50 µmHg (6.66 Pa), optionally between 30 and 35 µmHg (4.00 and 4.66 Pa) and time from 2 to 24 h.

In one embodiment, the freeze-drying occurs optionally at –55° C., pressure around 30 µmHg (4.00 Pa) and time of 3 h30 min for skins with a diagonal larger than up to 16 cm; 5 h for skins with a diagonal larger than up to 25 cm; optionally the skins are freeze-dried for sufficient time so that the residue humidity of the biological tissue is reduced up to 10-15%.

In one embodiment, in step (v) the sealing is carried out in plastic packaging with thickness from 0.15 to 0.20 µm.

In one embodiment, step (vi) occurs with gamma radiation generated by Cobalt 60 radiators and dosages between 5 and 50 kGy, optionally 25 kGy.

In one embodiment, step (vi) comprises optionally the sterilization of the skins by ultraviolet radiation, with wavelength varying between 210 and 330 nm and exposure time between 10 and 100 seconds.

As a second object, there is the animal skin, optionally fish, optionally freeze-dried tilapia obtained by the method described in the first object and embodiments thereof.

In a third object there is provided the use of the freeze-dried animal skin, optionally fish, optionally freeze-dried tilapia, for producing occlusive dressing materials for treatment in humans and animals comprised within the group: second and/or third degree burns, acute, chronic and traumatic wounds, battlefield wounds, skin donor areas for self-graft, vaginal and pelvic floor reconstruction, neovaginal construction, sexual reassignment for transgenders, reconstruction of nasal lining and of buccal cavity, gum reconstruction, tissue rupture, dermatitises, lacerations, abrasions, bruises, necrotizing fasciitis, toxic epidermic necrolysis (TEN), Stevens Johnson Syndrome, pressure wounds, ulcers due to venous insufficiency, vascular ulcers, diabetic ulcers or neuropathic, mixed ulcers, vasculitis wounds, gangrenous pyoderma, anal fistula, reconstruction of esophageal wall, facial reconstruction, mucormycosis, filling of oral mucosa, dental cavity and alveoli.

The present invention presents as a fourth object a kit comprising the animal skin, optionally fish, optionally freeze-dried tilapia.

EXAMPLES

The examples shown herein have the purpose only of exemplifying one of the countless ways to perform the invention, without however limiting the scope of the same.

Example 1—Obtaining the Freeze-Dried Tilapia Skin

Initially, the tilapias are obtained from fish farms, which use cultivation systems (tanks-net), passing through a sterilization method, as described below.

After the slaughter of the fish, the skins of the tilapia (weighing between 250 and 1500 g) will be removed and submitted to washing in hot water, for removal of any blood residue and other impurities and placed in sterile plastic boxes, in isothermal boxes with ice, for transport to the laboratory, where the following steps are carried out:

Step 1—Cleaning of the Skins

The cleaning of the skins is made with physiological saline solution (NaCl solution at 0.9%), removal of the excess muscle from the dermis and trimming of the skin edges.

Step 2—Incubation with Biocompatible Detergent in Sterile Recipient

The skins are placed in a sterile recipient containing 3-[(3-Cholamidopropyl)dimethylammonium]-1-propane-sulfonate (CHAPS), at 0.25%, where they will remain for 15 minutes and will be used in a repetition of this step, to subsequently be incubated in sterile distilled water for 25 minutes.

Step 3—Incubation in Sterile Recipient with Bactericidal Agent

The skins are placed in a sterile recipient, containing chlorhexidine digluconate at 0.05%, where they will remain for 60 minutes and will be incubated in sterile distilled water for 25 minutes.

Step 4—Incubation in Sterile Recipient with Detoxification Solution

The skins are placed in a sterile recipient, containing citric acid/citrate buffer 0.5 mol/L pH 6.0, where they will remain for 120 minutes and will be used in a repetition of this step, to subsequently be incubated in sterile distilled water for 15 minutes and in a repetition of this incubation.

Step 5—Rinsing and Freezing

The skins are rinsed in physiological saline solution and frozen between −20° C. and −196° C., for 8 to 24 h, in metallic tray, with the gray face (filled with melanophores) turned downwards. Optionally $N_2$ can be used for carrying out this freezing.

Step 6—Freeze-Drying

The frozen skins are added to a freeze-dryer at −30° C. to −80° C., with inner pressure lower than 50 μmHg (6.66 Pa), optionally between 30 and 35 μmHg (4.00 and 4.66 Pa), in an interval of time from 2 to 24 h, in a clean room, between 18° C. and 37° C., optionally at 25° C.

Step 7—Vacuum Sealing

After the time in the freeze-dryer the skins are removed from the freeze-dryer and packaged individually or in several units, in vacuum machines, in Clean Room Classification environment types 5 to 7, in appropriate plastic, with thickness from 0.15 to 0.20 μm.

Step 8—Sterilization

The dehydrated and vacuum-sealed skins are radio-sterilized with Gamma radiation generated in a Cobalt 60 radiator, with load dosages that vary between 5 to 50 kGy.

Optionally, the dehydrated skins can also be sterilized by ultraviolet radiation, with wavelength varying between 210 nm and 330 nm and exposure time between 10 to 100 seconds.

Example 2—Microbiological Tests

Microbiological tests were carried out for gram +, gram − bacteria and fungi, beginning with the skin in natura, that is, prior to the first step and in the steps described above. When the Bioburden levels, that are used for the bacterial count, that is the Bioburden Microbiological Analysis, or Microbial Limit Test, which is carried out in pharmaceutical products and medical products that require control of microbial levels during the processing and manipulation, are within the acceptable limits, the skin will be available for use.

The freeze-dried tilapia skin of the present invention was tested as to the in vitro toxicity, according to the ISO 10993-5 guideline. The skin was considered as being non-cytotoxic, since it allowed a cell viability higher than 75% in the cytotoxicity test by extract with lineage L929, derived from murine fibroblast. Subsequently, the freeze-dried skin was used in murine burn models, in comparison with the silver sulfadiazine cream. Apart from providing healing not inferior to that of the cream, the Tilapia skin provided a reduction of the pro-inflammatory cytokines in the site of the wound, revealing a pronounced anti-inflammatory action as regards the traditional treatment. Finally, clinical studies in voluntary burn victims have been initially started. The freeze-dried skin has shown itself to be an excellent alternative as regards the skin conserved in glycerol. All these results evidence the safety of the freeze-dried skin, however, the cited researches are in the final stages and require other analyses, such as histology and proteomic evaluations.

Example 3—Use of the Freeze-Dried Tilapia Skins

Additionally, the freeze-dried skin in the conditions that are standardized in this invention is capable of rapid macroscopic rehydration, which makes it more adequate for the use in medical and veterinary practice.

In a macroscopic rehydration execution, the rehydration occurs optionally in sterile physiological saline solution, at room temperature, by immersion in stainless steel hospital tray, wherein the volume of solution must be sufficient to immerse the skin in the physiological saline during optionally 15 minutes, without the need to agitate the tray.

The tilapia skin that is manufactured in the above described manner will be used in the medical and veterinary treatment of wounds, promoting the acceleration of the healing and wound repair methods (by Type I Collagen action existing in the histological structure thereof), due to the fact that it adheres to the wound bed, providing retention of exudates and avoiding the loss of liquids, providing a barrier against the bacterial invasion and providing pain relief.

Those skilled in the art will value the knowledge presented herein and can reproduce the invention in the embodiments presented and in other variants and alternatives, covered by the scope of the following claims.

The invention claimed is:

1. A method for obtaining a temporary occlusive biological dressing, characterized by comprising a following steps:

i) cleaning and trimming a tilapia skin, wherein the species of tilapia is *Oreochromis niloticus*;

ii) successive steps of incubation of the skin with biocompatible detergent or incubation with bactericidal agent or both incubation with a bactericidal agent and a biocompatible detergent followed by rinsing and/or incubation with detoxifying solution and rinsing with physiological saline solution; and iii) freeze-drying the tilapia skin at a temperature in the range of −30° C. to −80° C., with internal pressure between 4.00 and 4.66 Pa and for the time from 2 to 24 h;

wherein the biocompatible detergent is 3-[(3-cholamidopropyl)dimethylammonium]-1-propanesulfonate, or Polysorbate 20, or t-octylphenoxypolyethoxyethanol, or sodium deoxycholate or 4-nonylphenyl-polyethyleneglycol or a combination of these, wherein the bactericidal agent is chlorhexidine digluconate, or sodium chlorite, or cetylpyridinium chloride, or chloramine T and/or sodium dichloroisocyanurate or a combination of these; and wherein the detoxifying solution is acetic acid/acetate buffer, or glycine/HCl buffer, or citric acid/citrate buffer, or sodium monobasic phosphate/sodium dibasic phosphate buffer or a combination of these.

2. The method according to claim 1 characterized by comprising an additional step of freezing before step iii) of freeze-drying.

3. The method according to claim 1, characterized in that step (ii) of incubation with biocompatible detergent occurs in a sterile environment containing from 0.001 to 0.5% of detergent, for 15-60 minutes, in two to five repetitions, followed by two to five incubations with sterile distilled water in the same recipient for 15-60 minutes.

4. The method according to claim 1, characterized in that the incubation with bactericidal agent comprised in step (ii) occurs in sterile recipient containing bactericidal agent in the range from 0.005 to 1.0%, optionally 0.01-1%, for 15-60 minutes, followed by rinsing in sterile distilled water and incubation in sterile distilled water in the same recipient for 15 to 60 minutes, in two to ten repetitions.

5. The method according to claim 1, characterized in that step (iii) comprises freeze-drying for a time of 8 to 24 h.

6. The method according to claim 1, characterized in that step (iii) occurs in a freeze-dryer at –55° C., with inner pressure of 4.00 Pa and time of 3 h and 30 minutes.

7. The method according to claim 1, further comprising a step of sterilizing the fish skin, characterized in that the sterilization step occurs with gamma radiation generated by Cobalt 60 radiators and dosages between 5 and 50 kGy, optionally 25 KGy and optionally, the skins can be sterilized by ultraviolet radiations with wavelength varying between 210 and 330 nm and exposure time between 10 to 100 seconds.

8. The method according to claim 1, characterized by B comprising after the step iii) of freeze-drying additional step of vacuum sealing and sterilization.

9. The method according to claim 1, characterized in that, the incubation with detoxification solution comprised in step (ii) occurs in sterile recipient containing solution 0.025-0.50 mol/L, pH 3.0-6.0, for 30-120 minutes, in two to fifteen repetitions, followed by incubation with sterile distilled water in the same recipient for 15-60 minutes, in two to ten repetitions; followed by rinsing with physiological saline solution;

wherein the detoxification solution is acetic acid/acetate buffer, or glycine/HCl buffer, or citric acid/citrate buffer, or monobasic phosphate/dibasic sodium phosphate buffer or a combination of these.

10. The method according to claim 1 characterized in that in step (ii) the biocompatible detergent is 3-[(3-cholamidopropyl)dimethylammonium]-1-propanesulfonate (CHAPS); the bactericidal agent is chlorhexidine digluconate; the detoxification solution is glycine/HCl buffer and the physiological saline solution is a phosphate buffer saline solution.

* * * * *